United States Patent [19]

Vadnay et al.

[11] 4,341,538
[45] Jul. 27, 1982

[54] INTRAVENOUS FILTER

[75] Inventors: Attila Vadnay, Ann Arbor; Mary K. Boomus, Chelsea, both of Mich.

[73] Assignee: Gelman Instrument Company, Ann Arbor, Mich.

[21] Appl. No.: 934,957

[22] Filed: Aug. 18, 1978

[51] Int. Cl.³ .............................................. B01D 31/00
[52] U.S. Cl. ..................................... 55/159; 210/436; 210/445; 210/455
[58] Field of Search .................. 55/159, 178; 210/436, 210/445, 455, DIG. 13

[56] References Cited

U.S. PATENT DOCUMENTS 3,085,689 4/1963 Hering et al. ................... 210/445 X
3,295,297 1/1967 Collins ................................. 55/178
3,650,093 3/1972 Rosenberg .......................... 55/159
3,803,810 4/1974 Rosenberg .......................... 55/159
3,905,905 9/1975 O'Leary et al. ................. 55/159 X
4,009,714 3/1977 Hammer ........................ 210/445 X Primary Examiner—Charles N. Hart
Assistant Examiner—David R. Sadowski
Attorney, Agent, or Firm—Reising, Ethington, Barnard, Perry & Brooks

[57] ABSTRACT

A filter for intravenous solutions including a flat, rectangular housing formed of two pieces sandwiching a filter sheet diagonally from end to end with support ribs on one side of the sheet and luer connections in the large end of each piece of the housing.

2 Claims, 8 Drawing Figures

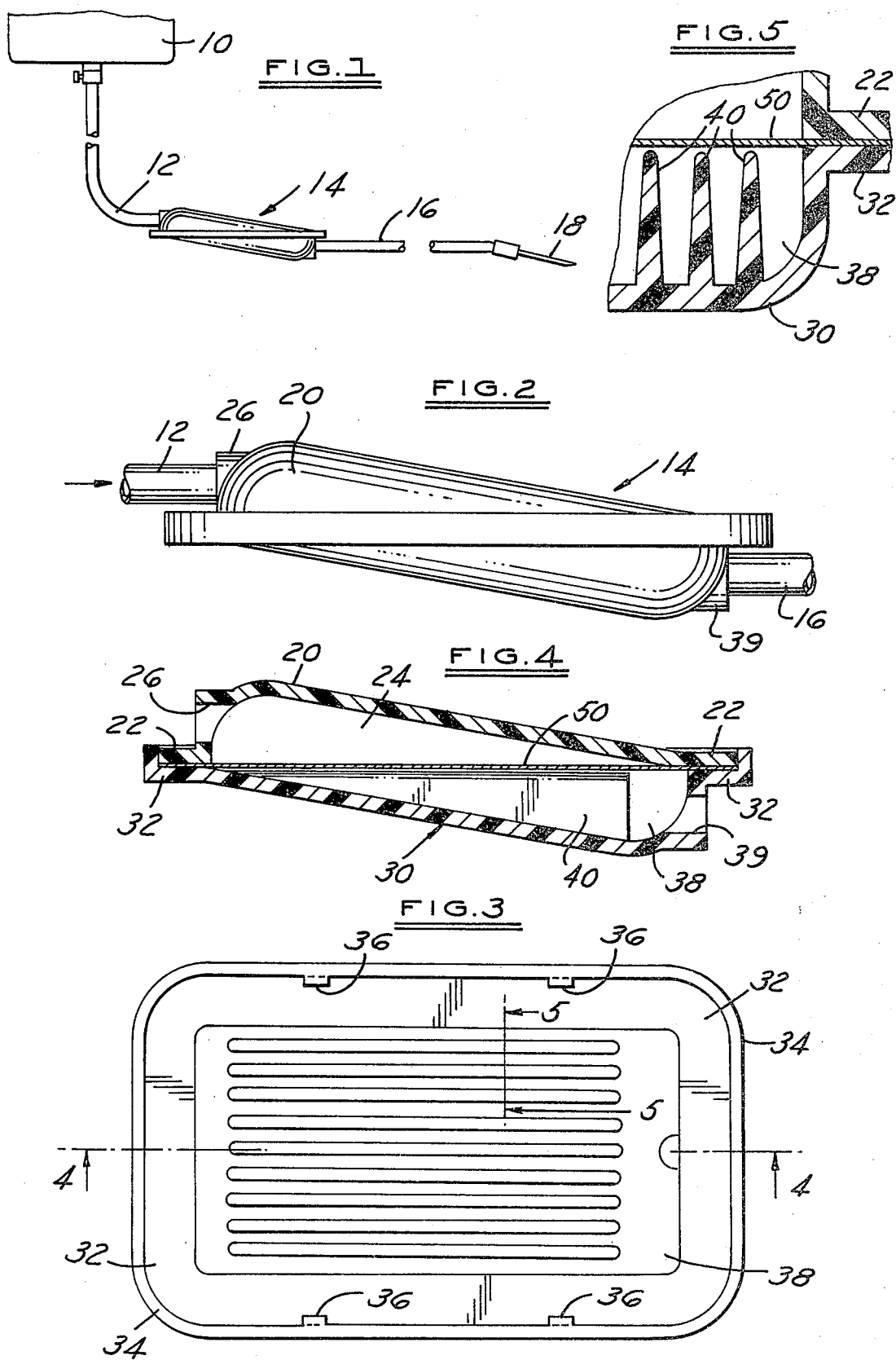

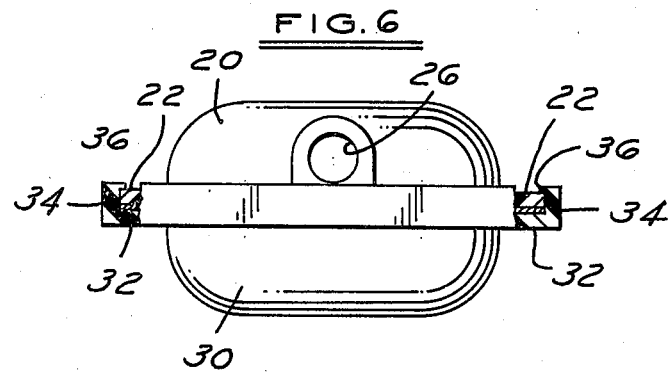
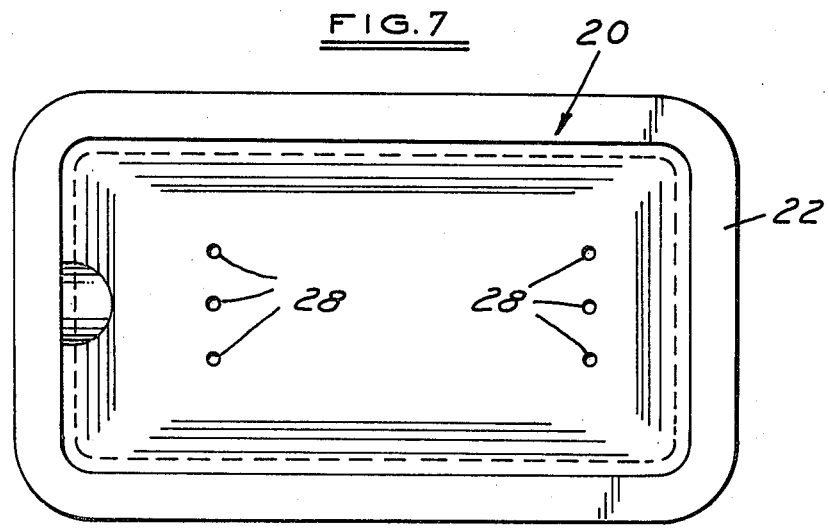
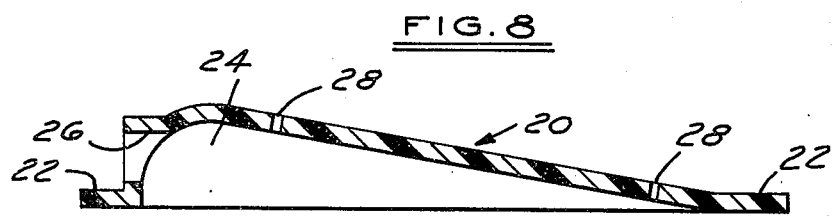

INTRAVENOUS FILTER

FIELD OF INVENTION

This invention relates to an intravenous filter and housing used to filter solutions administered to a patient intravenously and designed to be inserted in the tube leading from the intravenous supply bottle to the intravenous needle.

BACKGROUND

Intravenous filter housings have been utilized but have certain drawbacks. Filter area should be maximum and the luer connection should be such as to accomodate standard tubing. In addition, the housing should be of such a design that the filter sheet can be readily secured peripherally while properly supported mechanically during the filtering function. The device must also be inexpensive enough that it can be disposable.

OBJECTS OF THE PRESENT INVENTION

It is an object of the present invention to provide an intravenous filter which has a maximum filter area with the filter peripherally secured in a housing which provides mechanical support for the filter sheet and at the same time providing luer or solvent weld connections at the end without protruding enlargements or openings in the side faces of the housing. This permits in-line installation.

It is a further object to provide a filter design which minimizes air bubble formation and provides improved flow characteristics. It is another object to provide a filter housing which has an identical exterior shape on each side to simplify die construction for multiple production.

Other objects and features of the invention will be apparent in the following description and claims in which the best mode presently contemplated for the invention is set forth together with details of construction and operation.

BRIEF DESCRIPTION OF THE DRAWINGS

Drawings accompany the disclosure, and the various views thereof may be briefly described as:

FIG. 1, a view of the improved filter installed in an intravenous tube.

FIG. 2, a side view of the completed filter.

FIG. 3, a bottom view of the completed filter.

FIG. 4, a sectional view on line 4—4 of FIG. 3.

FIG. 5, a sectional view on line 5—5 of FIG. 3.

FIG. 6, an end view.

FIG. 7, a top view.

FIG. 8, a longitudinal section of FIG. 7.

DETAILED DESCRIPTION

With reference to the drawings, in FIG. 1, an intravenous bottle 10 is connected by a tube 12 to a filter housing 14 which in turn is connected by a tube 16 to an intravenous needle 18. In FIGS. 2, 3 and 4, enlarged views of the composite housing are shown wherein a top housing 20 has a flat peripheral flange 22 with a gradually rising top wall to provide an inlet chamber 24 which increases in height to the inlet end in which is formed an extended luer connection 26. The height of the housing at the enlarged end permits the formation of a luer connection without a special protuberance.

The top housing 20 may also be provided with air outlet openings 28 as shown in FIGS. 7 and 8.

The bottom housing 30 in FIGS. 2, 3 and 4 is formed with a flat peripheral flange 32 having an upstanding peripheral wall 34 which, in assembly, surrounds the flange 22 of the top housing as shown in FIG. 4. The side runs of the wall 34 have inwardly extending spaced tabs 36 which overlie flange 22 as shown in the sectional sides of FIG. 6.

The chamber or cavity 38 in the bottom housing 30 deepens as it progresses from left to right in FIGS. 2, 3 and 4 to the same degree that chamber 24 increases in height and also has spaced, rather thin, parallel ribs 40 (FIGS. 3 and 5) which extend longitudinally of the lower housing with top surfaces lying in a plane parallel to and slightly below the plane of the flange 32. The ribs terminate short of the end of chamber 38 and an extended luer connection 39 is formed at this end.

In the example shown, the overall dimension of the assembly is about 61 mm in length and 35.5 mm in width. The chambers are about 53 mm long and 28 mm wide with an outside maximum depth of 9 mm. The thickness of the ribs and the spacing of the ribs 40 is 1.34 mm at the base, and the top of the ribs are about 0.254 mm from the plane of the flange 32.

In assembly, a filtering membrane 50 may be a supported membrane such as "Acropor" manufactured by the Gelman Instrument Company of Ann Arbor, Mich., or a combination of a supported and non-supported membrane having a pore size with a 0.2 to 5 micron range depending on the application. The membrane is fitted over flange 32 of the lower housing and the top housing flange 22 is brought into contact with the periphery of the filter sheet to clamp it in place. The tabs 36 hold the parts in assembly and the flanges can then be fused together with a suitable heat sealing process.

In the operation of the device, the assembled unit can be connected into the tube system of an intravenous set up as shown in FIG. 1. The end connections 26 and 39 are permitted by the enlarged chambers with the filter membrane now diagonally positioned from cover to cover of a rectangular housing. These end connections permit an in-line assembly so that the unit may be taped on to the arm of a patient adjacent the needle insertion. The bottom side 30 is applied to the skin and forms a pre-warming chamber for the solution as it passes through the filter. If a filter is used which has vent openings 28 as shown in FIGS. 7 and 8, a hydrophobic membrane may be used to overlie these openings and permit the passage of air but not liquid to the openings.

The in-line flow pattern reduces turbulance and minimizes the air bubble formation in the unit.

We claim:

1. A filter housing and assembly for intravenous fluids which can be taped to the limb of a patient which comprises:
   (a) a bottom, rectangular, membrane-support housing having a peripheral flange lying in a plane, and a chamber within said flange descending from substantially no depth at one end to a maximum depth at the other end with a flat bottom surface to provide an elongate wedge-shaped chamber and a luer connection at said other end on an axis substantially parallel with said plane and extending in a direction of the major axis or said housing,
   (b) a top, rectangular, housing having a peripheral flange lying in said plane and shaped to mate with the peripheral flange of said bottom housing and a chamber within said flange having a maximum height at one end opposite to the end with the maximum depth of the bottom housing and decreasing to substantially no depth at the other end to provide a wedge-shaped elongate chamber with a luer connection formed at the end of maximum height on an axis parallel to the said plane and extending in a direction of the major axis of said housing whereby flow is in-line through the assembly from one end to the other, and (c) a filter membrane peripherally captured between said flanges to lie between said elongate chambers, whereby when said bottom housing is taped to the limb of a patient it conducts body heat to intravenous liquid passing through said filter membrane to said bottom housing.

2. A filter as defined in claim 1 in which said bottom housing has a plurality of parallel, spaced ribs extending longitudinally in the direction of the major axis of said chamber and having a common height extending from said flat bottom surface to a plane adjacent said membrane to provide spaced supports for said membrane which is carrying a liquid to be filtered through said filter membrane and administered intravenously to a patient on which the filter is mounted.

* * * * *